United States Patent [19]

Bach et al.

[11] Patent Number: 5,156,951
[45] Date of Patent: Oct. 20, 1992

[54] DETECTING IMMUNOLOGICAL CHANGES IN HIV INFECTED PATIENT SAMPLES

[75] Inventors: Bruce A. Bach, Alamo; Noel L. Warner, Los Gatos; Anne Jackson, Sunnyvale, all of Calif.

[73] Assignee: Becton Dickinson and Company, Franklin Lakes, N.J.

[21] Appl. No.: 379,127

[22] Filed: Jul. 13, 1989

[51] Int. Cl.⁵ .............................. G01N 33/53
[52] U.S. Cl. .................... 435/7.24; 435/7.1; 435/7.9; 435/7.92; 435/975; 435/5; 436/548
[58] Field of Search ........ 435/7.2, 7.24, 7.1, 435/7.9, 975, 5; 436/548

[56] References Cited

U.S. PATENT DOCUMENTS

| | | | |
|---|---|---|---|
| 3,826,364 | 7/1974 | Bonn et al. | 209/3 |
| 4,284,412 | 8/1981 | Hansen et al. | 23/230 |
| 4,452,773 | 6/1984 | Molday | 424/1.1 |
| 4,520,110 | 5/1985 | Stryer et al. | 436/501 |
| 4,607,007 | 8/1986 | Lanier et al. | 435/7.24 |
| 4,628,026 | 12/1986 | Gardell et al. | 435/7.24 |
| 4,661,913 | 4/1987 | Wu et al. | 364/500 |
| 4,677,061 | 6/1987 | Rose et al. | 435/7.24 |
| 4,717,655 | 1/1988 | Fulwyler | 435/7.24 |
| 4,727,020 | 2/1988 | Recktenwald | 435/6 |

OTHER PUBLICATIONS

Daniel et al: Lymphocyte autoantibodies . . . patients Clin Exp Immunol. 75(2) pp. 178–183 Feb. 89 Abstract Only!
Redfield et al., Sc. Amer., 259:70 (1980).
Vchiyana et al., J. Immunol., 126:1393 (1981).
Schulman et al., Natura, 276:269 (1978).
Herzenberg et al., Sci. Amer., 234:108 (1976).
Lewis et al., J. Infect. Diseases, 151:555 (1985).
Honda et al., J. Immunol., 142:4248 (1989).
Stites et al., Clin. Immunol. Immunopath., 38:161 (1986).
Clerici et al., Nature, 339:383 (1989).
Kohler et al., Eur. J. Immunol. 6:511 (1976).

Primary Examiner—Christine Nucker
Assistant Examiner—Jeffrey Stucker
Attorney, Agent, or Firm—Robert M. Hallenbeck

[57] ABSTRACT

The present invention comprises a method for detecting immunological changes in blood samples from patients infected with HIV. The method comprises the use of fluorescently labelled monoclonal antibodies against IL-2R (CD25). Other antibodies, including anti-CD3, anti-CD38 and anti-HLA DR antibodies also may be used. It has been found that a decrease in expression of CD25 in such samples indicates HIV infection.

8 Claims, 3 Drawing Sheets

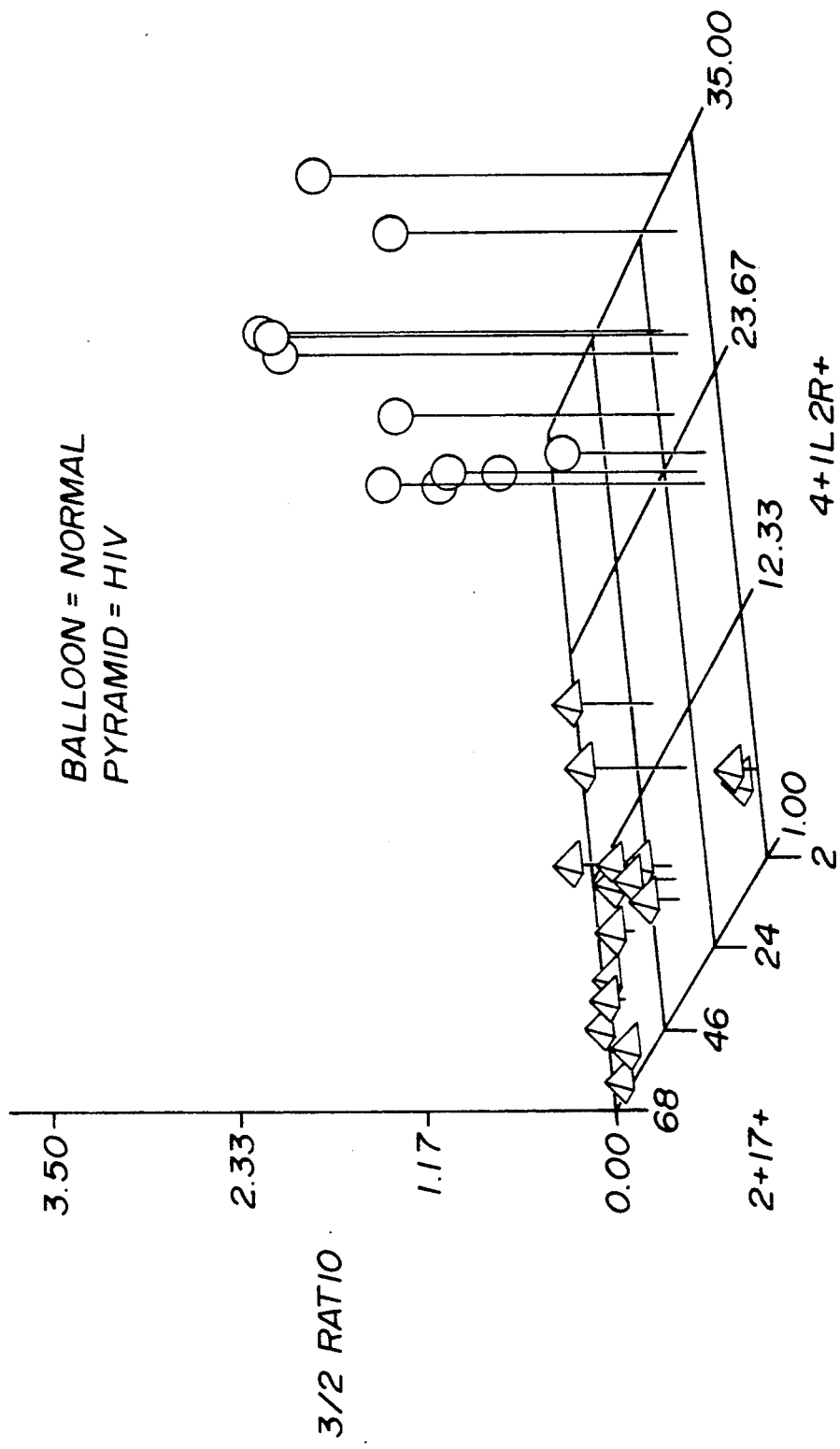

DETECTING IMMUNOLOGICAL CHANGES IN HIV INFECTED PATIENT SAMPLES

FIELD OF THE INVENTION

This invention relates to a novel assay for the detection of immunological changes associated with viral infection and more particularly relates to an assay involving the use of monoclonal antibodies against the interleukin-2 receptor ("IL-2R") for detecting immunological changes associated with human immunodeficiency virus ("HIV").

BACKGROUND OF THE INVENTION

AIDS is a clinically defined medical illness which can result from an infection with HIV. The definition of AIDS has been published and continually revised by the Centers for Disease Control (Atlanta). It is generally accepted that progression of the infection gradually renders the individual immunodeficient, and as a result, HIV leads to death from fatal opportunistic infections such as *Pneumocystis carinii* pneumonia. The mechanism by which HIV infection results in AIDS is believed to be mediated through the binding of HIV to a subset of T-cells (the T helper or "$T_h$" subset) which are identified by the CD4 and CD3 surface antigens. By infecting and subsequently destroying the $T_h$ subset of lymphocytes, the individual infected with HIV loses the ability to respond to certain infectious agents.

HIV infections progress through a number of different clinical stages which may be distinguished in both clinical and laboratory findings. One presently accepted classification system for defining and staging the progress of HIV infection from initial exposure through the diagnosis of AIDS is described in the Walter Reed Classification System. This system is set out in Table 1.

example, that at some point after infection many individuals make antibodies against HIV proteins and that these HIV antibodies are detectable in blood samples using, for example, recombinant or synthetic gp120 (an HIV viral envelope) as a capture antigen. This serum based method, however, assumes that the progression of the disease in the individual is to such a state that not only are antibodies being made against HIV but that the antibodies made by the individual will react with gp120 and in sufficient quantity so as to be detectable. Indeed, early antibody responses may be masked by the presence of free virus in the peripheral blood.

Similarly, using the reverse approach, antibodies against gp120 and other viral antigens (e.g., p24) may be made and used to detect the presence of virus or viral protein in a sample of blood from an individual. Although this is an antigen capture based method, its use assumes that the detecting antibodies will react will all forms of HIV which may be present in any particular infection and assumes that the viral particles are present in the serum sample, however. Virus particles are only transiently present in serum.

A further method for evaluating the serological response of an infected individual involves the use of the Western blotting technique wherein a serum sample derived from an individual is incubated with a piece of filter paper to which an electrophoretically separated preparation of HIV protein antigens have been fixed. If antibody is present in the serum sample then a precipitation product is generated and it may be assumed that antibodies are present to specific viral proteins. Again, this assay is based on the infected individuals serological response to the HIV virus.

Apart from these presently practiced techniques, other methods have been tried to identify HIV infection.

Changes in the number of cellular immune effectors

TABLE 1

| Stage | Ab/Virus | Chronic Lymphad-enopathy | $T_h$ Cells (cells/mm$^2$) | Delayed Hypersensitivity | Thrush | Opportunistic Infections |
|---|---|---|---|---|---|---|
| WR0 | − | − | >400 | Normal | − | − |
| WR1 | + | − | >400 | Normal | − | − |
| WR2 | + | + | >400 | Normal | − | − |
| WR3 | + | + | <400 | Normal | − | − |
| WR4 | + | + | <400 | Partial | − | − |
| WR5 | + | + | <400 | Complete and/or | + | − |
| WR6 | + | + | <400 | Complete | + | + |

As may be seen from Table 1, a number of separate criteria go into evaluating and defining each of the several stages. For example, the presence or absence of antibodies (Ab) to HIV or the presence or absence of detectable virus itself are used as an indication of initial exposure to HIV (WR1). Subsequently, the number of $T_h$ cells in the blood may be measured. As the number of $T_h$ cells falls, the farther the disease has progressed (WR3). For a further description of the Walter Reed Classification System and the clinical aspects of AIDS, see Redfield et al., Sci. Amer., 259:70 (1988).

While the Walter Reed Classification System provides a means for monitoring and staging the progress of an individual's disease the system is based, at least initially, on the ability to quantify the number of $T_h$ cells present in a sample and/or detect the presence of anti-HIV antibodies or virus in a sample. Unfortunately, currently available techniques for the detection of antibodies or virun have certain limitations. It is known, for such as the number of CD4+T cells or the ratio of CD4+/CD8+ cells also have been used to identify and stage HIV infection. As noted above, the number of CD4+T cells provides one basis for the Walter Reed Classification System. The ratio of CD4+/CD8+ cells also may be indicative of the progression of the HIV infection. Finally, still other studies have reported that with HIV infection the number of HLA-DR+T cells or the number of CD8+/CD38+ cells increases.

Because of the variable time course of appearance of certain of these markers and because of the potential unreliability of a number of these presently practiced techniques and often, a number of these techniques are used in concert in order to determine whether an individual has been exposed to HIV and has either made an antibody response or has the virus in the blood. This approach is both costly and time consuming. Accordingly, a rapid/early and reliable means for detection of HIV infection is needed.

SUMMARY OF THE INVENTION

The present invention comprises a novel assay for the detection of immunological changes associated with a viral infection, and in particular with an HIV infection, which is not limited by the clinical stage of the individual. Changes in immunological status may be indicative of HIV infection.

The assay comprises a method for rapidly determining the number of IL-2R+ lymphocytes present in a sample. Surprisingly, it has been found that the number of IL-2R+ cells in normal individuals is approximately 30% and that this value significantly decreases with the onset of HIV infection. In particular, a decrease in the number of IL-2R+ T cells correlates highly with HIV infection. Accordingly, by labelling IL-2R+ cells in a sample, particularly lymphocytes and more particularly T cells, the number of IL-2R+ cells can be counted and compared against a normal range of values. In addition, the number of CD38+ and HLA-DR+ T cells can be counted in the same sample and all three parameters may be used to identify HIV infected individuals. The information also is useful in staging the progression of HIV infection.

BRIEF DESCRIPTION OF THE DRAWINGS

FIG. 2 is a plot of the number of CD8+/CD38+ cells in a sample of lymphocytes obtained from normal and HIV positive individuals versus the number of CD3+/CD25+ cells versus the ratio of CD4+ to CD8+ cells in the sample.

DETAILED DESCRIPTION OF THE INVENTION

Figure 1B:
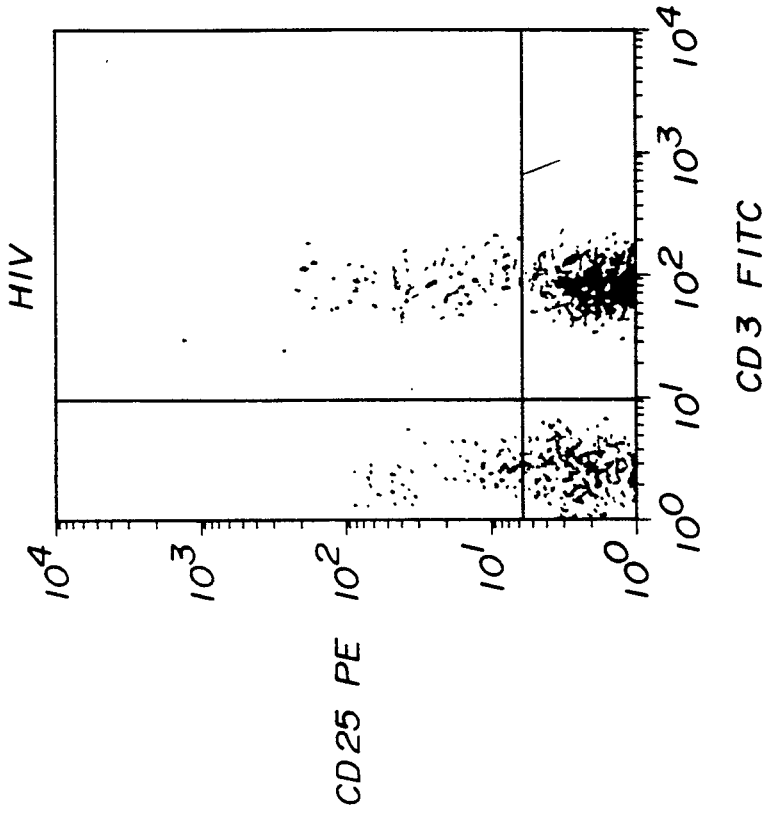
FIG. 1 is a dot plot of log fluorescence (anti-CD3 FITC and anti-CD25 PE) for peripheral blood lymphocytes obtained from (A) normal and (B) HIV positive individuals.

The present invention comprises a method of determining whether an individual has been exposed to a virus, particularly HIV, which results in immunological changes in the individual. In this method, a blood or other sample is collected from an individual. The sample then is treated to identify the cells expressing IL-2R. The treated cells then are analyzed by means capable of discriminating between cells expressing IL-2R and cells lacking IL-2R and counting the IL-2R+ cells. The number of cells expressing IL-2R then is compared to a range of standard values of a normal population. Preferentially, the number of lymphocyte cells expressing IL-2R is counted. Most preferentially, the number of T cells expressing IL-2R is counted.

In this method, preferentially, the sample comprises peripheral whole blood. Peripheral whole blood may be further treated to remove erythrocytes by means of lysis (leaving only leukocytes) or may be further treated by means of density gradient separation to prepare mononuclear cells (i.e., lymphocytes and monocytes). Alternatively, leukocytes or T cells may be isolated from peripheral whole blood by means of magnetically activated cell separation. In this procedure, magnetic microspheres of the type described in U.S. Pat. No. 4,452,773 are conjugated to a CD45 pan-leukocyte antibody, such as Anti-HLe-1 (Becton Dickinson Immunocytometry Systems, BDIS), or an anti-CD3 antibody such as Anti-Leu 4 (BDIS). The antibody/magnetic bead conjugate then may be mixed with the fluid sample and poured through and over the column containing a magnet. Cells bound to antibody will be retained in the column while cells not bound will be passed through. By removing the column from the permanent magnet, leukocytes or T cells can be collected.

Whether prepared by erythrocyte lysis or when collected by density dependent centrifugation, mononuclear cells and T cells therein may be identified by tagging agents such as antibodies, preferentially monoclonal antibodies. Monoclonal antibodies against CD3 may be prepared by the methods of Kohler and Milstein (below) or may be obtained commercially as, for example, Anti-Leu 4. It should be noted that this step could be omitted if T cells were initially isolated from peripheral blood by means such as magnetically activated cell sorting.

T cells expressing IL-2R may be identified in the sample by means of treating the sample with antibodies, preferentially monoclonal antibodies, directed against the CD25 (or TAC) antigen. IL-2R+ cells are by convention cells which express the CD25 antigen. The CD25 antigen is expressed on a significant percentage of normal resting unstimulated lymphocytes, but is detected at higher densities on activated T and B cells and on certain leukemic cells. The CD25 antigen is a protein which comprises the p55 subunit of the IL-2R. A second subunit (designated p75) recently has been shown to have an intermediate affinity for IL-2 and only when both the p55 and p75 subunits are both present on a cell is a high affinity receptor for IL-2 found. (The "CD" designation is the internationally accepted standard by which leukocyte antigens and antibodies thereto are classified.)

Monoclonal antibodies against IL-2R, and specifically against the CD25 antigen portion thereof, have been prepared by a number of persons, including Uchiyama et al., J. Immunol., 126:1393 (1981) (Anti-TAC), and also are commercially available from (BDIS) as Anti-IL-2R (clone 2A3). Other Anti-CD25 monoclonal antibodies may be made by conventional hybridoma technologies, such as those described by Kohler and Milstein, Nature, 276:269 (1978), using activated T cells as the immunogen. Clone 2A3, for example, was made by immunizing BALB/c mice with phytohemagglutin activated T cells and fusing their spleen cells with the mouse myeloma cells line NS-1 (ATCC TIB 18).

In order to identify cells bearing CD3 and/or CD25, the antibodies used to treat the cells are conjugated to fluorescent labels which have different emission spectra but, preferentially, are excitable at the same wavelength of excitation. Two labels having these properties are fluorochromes Fluorescein isothiocyanate (FITC) and R-phycoerythrin (PE). Other pairs of fluorochromes may be selected from the group consisting of FITC, phycoerythrin, Texas red (Molecular Probes), C-phycocyanine, allo-phycocyanine, and peridin-chlorophyll complex (BDIS).

Cells treated with the fluorochrome conjugated monoclonal antibodies then are examined using means to excite the fluorochromes present and to detect the fluorochrome emissions. Preferentially, such means comprise a flow cytometer wherein treated cells are passed substantially one at a time through a sensing region where light of excitation wavelength illuminates each cell and further wherein scattered light and fluorescence emitted by each cell is collected, recorded and stored in associated hardware and software. The emission and light scatter data so recorded for each cell then may be analyzed by means of differential fluorescence intensities for each of the cell types treated. In the most preferred embodiment, the percentage of CD3− cells that are also CD25+ is compared with a range of normal values for such double positive cells as determined by flow cytometry.

Flow cytometry provides an efficient and quantitative means for identifying and counting cells in a heterogeneous population derived from blood or other tissue components (i.e., CSF, urine, bone marrow or isolated tissue). In this method, anti-CD25 monoclonal antibodies labelled with a fluorochrome are mixed with a blood sample which then is prepared for analysis by a flow cytometer. (Less efficient and less quantitative means of identifying labelled cells include the use of fluorescence light microscopy.)

Flow cytometry and flow cytometers generally are described in U.S. Pat. Nos. 4,661,913, 4,284,412, and 3,826,364, and in an article by Herzenberg et al., Sci. Am., 234: 108 (1976). In principle, they operate to identify different populations of leukocytes in a heterogeneous sample by detecting multiple independent parameters on the individual cells that pass through a sensing region substantially one at a time. The sensing region essentially comprises an area illuminated by the light of a single wavelength and from which light is collected by an array of photomultiplier tubes. Each photomultiplier tube measures a separate parameter. Typically, these parameters include forward light scatter (or FLS, which is a measure of relative particle size), orthogonal light scatter (or OLS, which is a measure of relative granularity or spectral complexity) and fluorescence emissions (generally referred to as FL1, etc.)

Fluorescence may be measured from cells that incorporate a nucleic acid stain and/or may be measured from cells bearing surface markers which are labelled with monoclonal antibodies which have been conjugated directly or indirectly with fluorochromes. One method for conjugation of PE is described in U.S. Pat. No. 4,520,110. In the indirect method second antibodies, for example, fluorescently labelled goat anti-mouse antibodies are used as a second step reagent to detect the presence of the mouse derived primary monoclonal antibodies which react with the cellular antigen of interest. Fluorochromes and stains may be referred to as fluorescent labels.

It is important that if more than one fluorescent label is used that each label have a different wavelength of emission in order that fluorescence emission from each will minimally overlap. Generally, FITC and PE meet this criteria and are used. It is preferable that the labels also be excitable at the same wavelength. This allows the cells to be in the sample to be passed through one sensing region and exposed to light of a single wavelength (e.g., from an argon laser at 488 nm). In other embodiments, the flow cytometer may have more than one sensing region. In one such embodiment, a dual laser source may be used where the labels selected are not excitable at the same wavelength.

Separate detector channels within the flow cytometer are able to sense light emitted or scattered for each of the various cell parameter measurements. In a typical configuration four or more parameters are measured (e.g., FLS, OLS, FL1 & FL2). Signals from these detectors for each cell passing through the sensing region are collected and may be stored by appropriately equipped recording means and software (e.g., Consort 30 software or FACScan Research Software, BDIS). By combining and comparing these parameters, the various leukocyte components may be identified and distinguished. U.S. Pat. No. 4,727,020 provides one example of how a flow cytometer may be used in this method to obtain leukocyte differentials from blood.

In order to identify CD25+T cells, fluorescently labelled monoclonal antibodies against both CD25 and CD3 have been used. (CD3 is a lineage specific surface antigen expressed on virtually all T cells.) By using monoclonals conjugated with fluorochromes that fluoresce at different wavelengths, cells that express CD25 alone, CD3 alone, both CD3 and CD25 antigens can be identified and counted. Thus, CD3+/CD25− cells, CD3−/CD25+ cells and CD3+/CD25+ cells can be separately counted. Using this method, it generally has been accepted that less than 10% of T cells are CD25+ in a sample of blood from a "normal" individual (i.e., less than 10% of CD3+ cells also are CD25+). It recently has been discovered using high resolution flow cytometry that the true range for CD25+T cells in a sample of normal blood is on the order of 30%, not 10%.

A change from FITC to PE and a change from the type of optics used in cell sorters described in U.S. Pat. No. 3,826,364, have resulted in the ability of currently commercially available flow cytometers to detect antigens which are present in low density of copy number per cell. Instruments such as the FACScan brand flow cytometer (BDIS) which embody flow-through optics as described in FACScan User's Guide, Appendix C (BDIS) when used with PE labelled anti-CD25 monoclonal antibodies and FITC labelled anti-CD3 monoclonal resulted in the ability to detect a greater number of CD25+T cells in a sample. The improved ability to detect CD25+ cells in a sample when combined with the observation that with the onset of an HIV infection, and throughout the course of infection, the number of CD25+T cells present in a sample decreases significantly, provides a new cell based assay for the detection of HIV infection and for the stratification of disease progression.

In addition to counting the number of IL-2R+ cells in a sample, one or more of the following cell types or ratios also can be counted or determined and combined with the number of IL-2R+ cells as a more discriminating measure of HIV infection. In this embodiment, CD38+ and/or HLA-DR+ cells can be counted and/or the ratio of CD4+/CD8+ cells can be determined. CD38 and HLA-DR are cells surface antigen activation markers. CD38 is distributed on normal lymphocytes but expression is increased on activated T cells. HLA-DR is distributed on B cells, monocytes and activated T cells expressing class II major histocompatibility antigens.

In order to determine normal values, normal blood (i.e., blood which reacts negatively for HIV in an ELISA system) was collected in an evacuated tube containing ethylenediaminetetracetate ($K_3$). Aliquots of whole blood then were treated at room temperature for 15-30 minutes with Anti-Leu 4 FITC (BDIS) and Anti-IL-2R PE (BDIS). The treated cells were washed once in Dulbecco's phosphate buffered saline (without $Ca^{2+}$ and $Mg^{2+}$) and subjected to erythrocyte lysis, washed and in turn fixed in 0.5% paraformaldehyde in phosphate buffered saline. Treated cells were then analyzed on a FACScan brand flow cytometer equipped with a 15 mW argon laser. List mode data was stored and analyzed using Consort 30 software. Lymphocytes were identified by gating on FLS and OLS. Subsets of lymphocytes were examined as follows: T cells were examined using an anti-CD3 antibody, Anti-Leu 4 (BDIS); $T_h$ cells were examined using an anti-CD4 antibody, Anti-Leu 3a (BDIS); $T_c$ cells were examined using an anti-CD8 antibody, Anti-Leu 2a (BDIS); B cells were examined using an anti-CD 19 antibody, Anti-Leu 12 (BDIS) and NK cells were examined using an anti-CD16 antibody, Anti-Leu 11 (BDIS). All of these antibodies were fluorescently labelled with FITC. Table 2 sets forth the percentages of normal lymphocytes that express IL-2R for 10 individuals. The mean value for IL-2R+ cells in peripheral blood was approximately 31%. On IL-2R+ cells, the mean value for CD4+ expression was 65%. On IL-2R+ cells, the mean value for CD3+ expression was 85%. Thus, while IL-2R is expressed on a number of types of lymphocytes, the majority of IL-2R is expressed on CD4+ T cells.

Figure 1A:
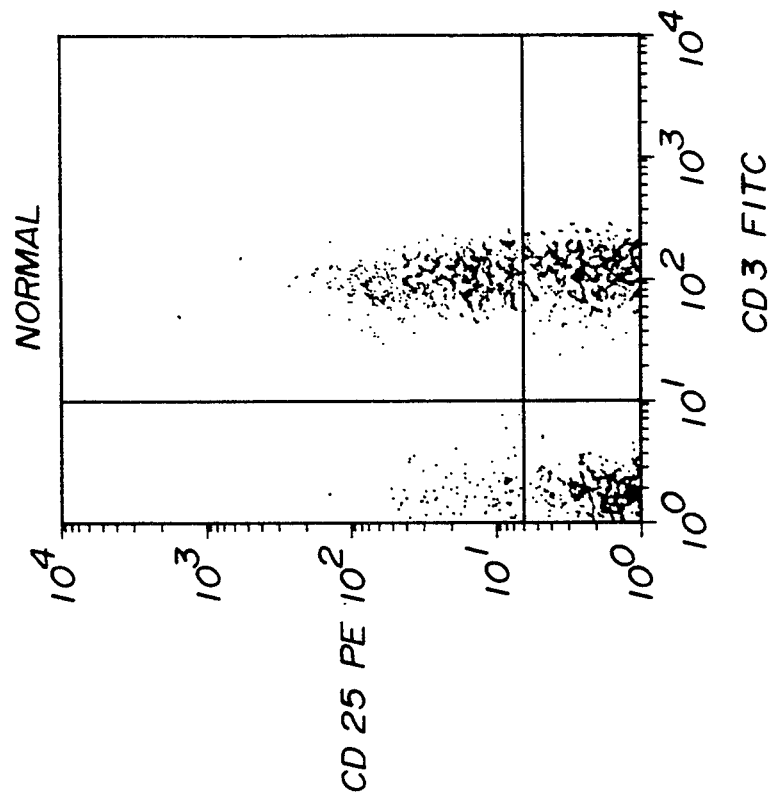

10% level previously reported. Surprisingly, the percentage of CD3+/CD25+ cells taken from HIV− individuals is significantly lower than those of normal. Accordingly, antibodies directed against CD25 are able to discriminate between normal individuals and individuals infected with HIV. Comparing FIG. 1(A) with 1(B) graphically demonstrates the difference between the several populations of normal from HIV infected cells where in Quad 1 contains CD3−/CD25+ cells, Quad 2 contains CD3+/CD25+ cells, Quad 4 contains CD3+/CD25− cells and Quad 3 contains double negative cells.

In addition to the use of anti-CD3 and anti-CD25 monoclonal antibodies to discriminate between normal individuals and HIV infected individuals, other antibody subsets may be run on aliquots of the same individual's blood to further discriminate between normal and HIV infected persons. Referring to FIG. 2, three aliquots of peripheral whole blood were taken from each individual. One aliquot was treated with Anti-Leu 4 and Anti-IL-2R (CD3/CD25) as discussed above. The other two aliquots were treated with Anti-Leu 2/Anti-Leu 17 (CD8/CD38) and Anti-Leu 3a/Anti-Leu 2 (CD4/CD8). The samples again were run on a FACS brand flow cytometer as above.

TABLE 2

Percentage of lymphocyte subsets which are IL-2R positive
Numerator = Percentage of IL-2R positive for each subset
Denominator = Total Percentage of Lymphocytes which are positive

| Donor | IL-2R Total Average | $\frac{CD3^+ \; IL\text{-}2R^+}{Total \; CD3^+}$ | $\frac{CD4^+ \; IL\text{-}2R^+}{Total \; CD4^+}$ | $\frac{CD8^+ \; IL\text{-}2R^+}{Total \; CD8^+}$ | $\frac{CD16^+ \; IL\text{-}2R^+}{Total \; CD16^+}$ | $\frac{CD19^+ \; IL\text{-}2R^+}{Total \; CD19^+}$ |
|---|---|---|---|---|---|---|
| 1 | 35 | 30/75 | 24/42 | 5/35 | 1/12 | 2/7 |
| 2 | 31 | 27/79 | 21/42 | 6/36 | 2/17 | 1/3 |
| 3 | 37 | 27/72 | 24/43 | 3/35 | 2/14 | 3/8 |
| 4 | 38 | 32/69 | 25/41 | 8/36 | 1/16 | 4/14 |
| 5 | 33 | 23/69 | 20/38 | 3/39 | 1/16 | 7/16 |
| 6 | 18 | 14/57 | 12/37 | 1/34 | 3/28 | 3/16 |
| 7 | 35 | 28/81 | 25/46 | 4/33 | 1/5 | 4/12 |
| 8 | 26 | 23/81 | 16/43 | 10/36 | 2/11 | 3/11 |
| 9 | 37 | 29/76 | 23/45 | 6/35 | 1/11 | 5/12 |
| 10 | 19 | 13/79 | 12/41 | 10/41 | 0/6 | 2/10 |

Mean 31 = 7
(±1 S.D.)

Based on this sample, it is apparent that either as a percentage of total lymphocytes or as a percentage of all T cells, the percentage of CD25+ cells in a sample far exceeds the 10% value previously recognized. The results of Table 2 are further confirmed in Table 3 on peripheral blood lymphocytes prepared by lysed whole blood technique, the samples were taken from HIV+ and normal individuals. In Table 3, the percentage of lymphocytes that are CD3−/CD25+ again exceed the Referring to FIG. 2, it can be seen that using the ratio of CD4 to CD8 cells in the sample in combination with the percentage of CD8+/CD38+ and CD3+/CD25+ cells, it is possible to make an additional distribution between normal individuals and HIV infected individuals.

Figure 3:
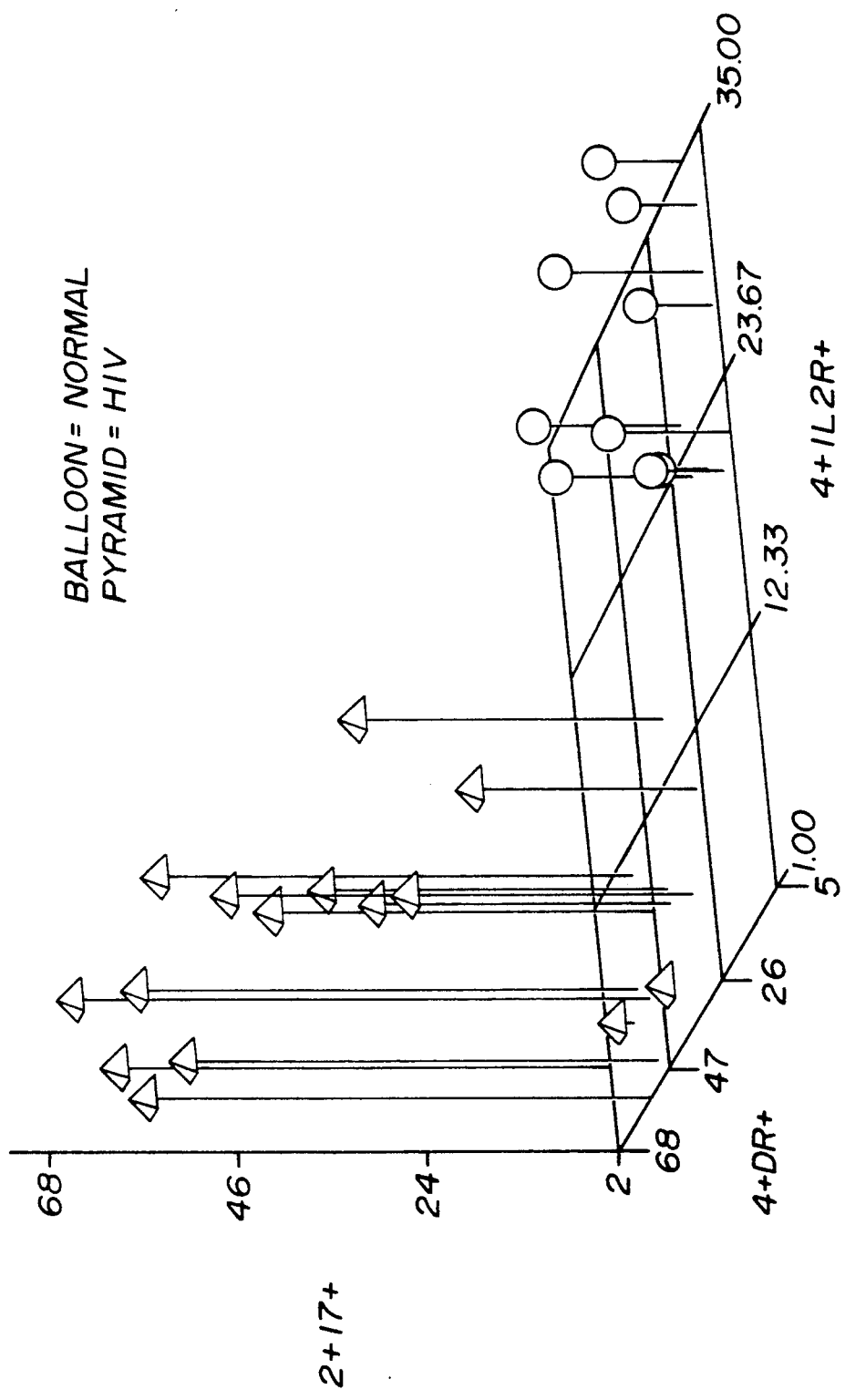
FIG. 3 is a plot of the number of CD8+/CD38+ cells in sample of lymphocytes isolated from nomal and HIV positive individuals versus the number of CD3+/CD25+ cells versus the number of CD3+/HLA-DR+ cells in the sample.

Referring to FIG. 3, three different aliquots from the same samples used above were stained using a lysed whole blood technique, however, in one aliquot Anti-Leu 4 was combined with Anti-HLA-DR. As in FIG. 2, the combination of CD8−/CD38−, CD3−/HLA-DR− and CD3+/CD25+ taken together are able to clearly discriminate and distinguish between blood taken from normal individuals and HIV infected individuals.

TABLE 3

QUADRANT TOTALS FROM THE 4/IL2R TUBE

| OBS | PATSTAT | PATID | QUAD1 | QUAD2 | QUAD4 |
|---|---|---|---|---|---|
| 1 | HIV | 001 | 3 | 5 | 59 |
| 2 | HIV | 002 | 4 | 9 | 73 |
| 3 | HIV | 003 | 12 | 12 | 59 |
| 4 | HIV | 004 | 3 | 4 | 50 |
| 5 | HIV | 005 | 8 | 7 | 46 |
| 6 | HIV | 006 | 1 | 6 | 73 |
| 7 | HIV | 007 | 2 | 15 | 69 |
| 8 | HIV | 008 | 2 | 2 | 73 |
| 9 | HIV | 009 | 2 | 10 | 77 |
| 10 | HIV | 010 | 2 | 7 | 62 |
| 11 | HIV | 011 | 3 | 11 | 82 |
| 12 | HIV | 012 | 1 | 5 | 76 |
| 13 | HIV | 014 | 2 | 5 | 82 |
| 14 | HIV | 015 | 2 | 6 | 77 |
| 15 | HIV | 017 | 3 | 8 | 67 |
| 16 | HIV | 018 | 4 | 5 | 74 |
| 17 | HIV | 019 | 2 | 7 | 71 |
| 18 | HIV | 020 | 3 | 5 | 82 |
| 19 | HIV | 021 | 3 | 8 | 68 |
| 20 | HIV | 022 | 2 | 14 | 79 |
| 21 | HIV | 023 | 3 | 2 | 86 |
| 22 | HIV | 024 | 1 | 5 | 85 |
| 23 | HIV | 025 | 2 | 1 | 84 |
| 24 | NORMAL | 001 | 7 | 34 | 43 |
| 25 | NORMAL | 002 | 3 | 17 | 65 |
| 26 | NORMAL | 003 | 4 | 22 | 52 |
| 27 | NORMAL | 004 | 8 | 24 | 54 |
| 28 | NORMAL | 005 | 7 | 23 | 48 |
| 29 | NORMAL | 006 | 13 | 18 | 24 |
| 30 | NORMAL | 007 | 7 | 21 | 55 |
| 31 | NORMAL | 008 | 3 | 18 | 65 |
| 32 | NORMAL | 010 | 4 | 21 | 65 |
| 33 | NORMAL | 011 | 6 | 25 | 42 |
| 34 | NORMAL | 012 | 3 | 27 | 48 |
| 35 | NORMAL | 015 | 5 | 20 | 48 |
| 36 | NORMAL | 016 | 6 | 35 | 43 |
| 37 | NORMAL | 017 | 12 | 32 | 45 |
| 38 | NORMAL | 018 | 6 | 29 | 39 |
| 39 | NORMAL | 020 | 6 | 22 | 62 |
| 40 | NORMAL | 021 | 6 | 25 | 55 |
| 41 | NORMAL | 022 | 6 | 21 | 55 |
| 42 | NORMAL | 023 | 4 | 21 | 63 |
| 43 | NORMAL | 024 | 4 | 27 | 39 |
| 44 | NORMAL | 025 | 7 | 21 | 46 |
| 45 | NORMAL | 172 | 5 | 17 | 58 |
| 46 | NORMAL | 173 | 9 | 25 | 54 |
| 47 | NORMAL | 175 | 6 | 25 | 49 |
| 48 | NORMAL | 177 | 3 | 20 | 45 |
| 49 | NORMAL | 178 | 5 | 17 | 57 |
| 50 | NORMAL | 179 | 8 | 16 | 53 |
| 51 | NORMAL | 180 | 7 | 16 | 52 |
| 52 | NORMAL | 181 | 5 | 16 | 66 |
| 53 | NORMAL | 182 | 5 | 13 | 60 |

| VARIABLE | MEAN | N | MINIMUM VALUE | MAXIMUM VALUE | RANGE |
|---|---|---|---|---|---|
| | | PATSTAT = HIV | | | |
| QUAD2 | 6.91304348 | 23 | 1.00000000 | 15.00000000 | 14.00000000 |
| | | PATSTAT = NORMAL | | | |
| QUAD2 | 22.26666667 | 30 | 13.00000000 | 35.00000000 | 22.00000000 |

Although the experiments performed in FIGS. 2 and 3 were run on separate aliquots of blood from the same individuals, it will be appreciated that three or more fluorescently labelled tagging agents may be used on a single aliquot. In this embodiment, an anti-CD25 antibody and one or more antibodies reactive with CD38, HLA-DR, T cells or T cell subsets may be used. Specifically, such combinations could include: anti-CD25, anti-CD38 and anti-HLA-DR; anti-CD25, anti-CD3 and anti-CD38; anti-CD25, anti-CD8 and anti-CD38; or anti-CD25, anti-CD38 and anti-CD4. As previously noted, all fluorescent labels must have separately distinguishable emmission peaks. They also may be excitable by a single light source.

All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed is:

1. A method for detecting changes in the expression of CD25 antigen on T cells in a sample of peripheral whole blood from an individual suspected of having an HIV infection comprising the steps of:
   a) obtaining a sample of peripheral whole blood from an individual suspected of having an HIV infection;
   b) treating the sample to provide a population of mononuclear cells;
   c) treating the population of mononuclear cells with a first fluorescently labelled monoclonal antibody that reacts with the CD25 antigen and with a second fluorescently labelled monoclonal antibody that reacts with the CD3 antigen wherein the fluorochromes have emission wavelengths that are distinguishable from each other;
   d) analyzing the cells by means of flow cytometry wherein light scatter and fluorescence are recorded for each of the cells analyzed; and
   e) counting the number of CD3+ cells in the sample that are CD25+, counting the number of CD3+ cells in the sample and determining the percentage of CD25+ T cells.

2. The method of claim 1 wherein one fluorochrome is fluorescein isothiocyanate.

3. The method of claim 1 wherein one fluorochrome is R-phycoerythrin.

4. The method of claim 1 wherein the sample of step b) is divided into more than one aliquot and wherein step c) is carried out on one aliquot and wherein a second aliquot is treated with fluorescently labelled monoclonal antibodies that react with CD8 and CD38.

5. The method of claim 1 wherein the sample of step b) is divided into more than one aliquot and wherein step c) is carried out on one aliquot and wherein a second aliquot is treated with fluorescently labelled monoclonal antibodies that react with CD3 and HLA-DR.

6. The method of claim 1 wherein the sample of step b) is divided into more than one aliquot and wherein step c) is carried out on one aliquot and wherein a second and third aliquot are treated with fluorescently labelled monoclonal antibodies that react with CD8 and CD38, and CD3 and HLA-DR respectively.

7. A method for detecting changes in the expression of CD25 antigen on CD3+ T cells in a sample of peripheral whole blood from an individual suspected of having an HIV infection comprising the steps of:
   a) obtaining a sample of peripheral whole blood from an individual suspected of having an HIV infection;
   b) treating the sample to provide a population of mononuclear cells;
   c) separating the population of cells into at least three aliquots;
   d) treating the first aliquot with a fluorescently labelled monoclonal antibody that reacts with the CD25 antigen and with a fluorescently labelled monoclonal antibody that reacts with the CD3 antigen, treating the second aliquot with a fluorescently labelled monoclonal antibody that reacts with the CD8 antigen and with a fluorescently labelled monoclonal antibody that reacts with the CD38 antigen, treating the third aliquot with a fluorescently labelled monoclonal antibody that reacts with the CD3 antigen and with a fluorescently labelled monoclonal antibody that reacts with the HLA-DR antigen, wherein each pair of antibodies are labelled with fluorochromes having emission wavelengths that are distinguishable from each other;
   e) analyzing the cells by means of flow cytometry wherein light scatter and fluorescence are recorded for each of the cells analyzed; and
   f) counting the number of CD3+ cells in the first aliquot and counting the number of CD3+ cells in that aliquot that are also CD25+, counting the number of CD8+ cells in the second aliquot and counting the number of CD8+ cells in that aliquot that are also CD38+, and counting the number of CD3+ cells in the third aliquot and counting the number of CD3+ cells in that aliquot that are also HLA-DR+ and determining the percentage of CD25+, CD38+ and HLA-DR+ T cells in each aliquot respectively.

8. The method of claim 7 wherein step b) further comprises preparing a fourth aliquot, step c) further comprises treating the fourth aliquot with a fluorescently labelled monoclonal antibody that reacts with the CD4 antigen and with a fluorescently labelled monoclonal antibody that reacts with the CD8 antigen, and step e) further comprises counting the number of CD4+ cells in the fourth aliquot and counting the number of CD4+ cells in that aliquot that are also CD8+ and determining the ratio of CD4+ to CD8+ cells.

* * * * *